United States Patent [19]
Ericksen et al.

[11] Patent Number: 5,891,043
[45] Date of Patent: Apr. 6, 1999

[54] IMPLANTABLE MEDICAL DEVICE WITH AUTOMATED LAST SESSION IDENTIFICATION

[75] Inventors: James H. Ericksen, Roseville, Minn.; Eric V. Eisinger, Hudson, Wis.; Jay R. Carey, Champlin, Minn.

[73] Assignee: Medtronic, Inc., Minneapolis, Minn.

[21] Appl. No.: 15,125

[22] Filed: Jan. 29, 1998

[51] Int. Cl.$^6$ .................................................. A61B 5/02
[52] U.S. Cl. ............................................. 600/508; 607/27
[58] Field of Search ............................. 607/27, 30, 10; 600/308, 310

[56] References Cited

U.S. PATENT DOCUMENTS

| B1 880,005 | 10/1996 | Pless et al. . |
| 4,316,472 | 2/1982 | Mirowski et al. . |
| 4,375,817 | 3/1983 | Engle et al. . |
| 4,384,585 | 5/1983 | Zipes . |
| 4,557,266 | 12/1985 | Schober . |
| 4,577,633 | 3/1986 | Berkovits et al. . |
| 4,587,970 | 5/1986 | Holley et al. . |
| 4,726,380 | 2/1988 | Vollmann et al. . |
| 4,727,877 | 3/1988 | Kallok . |
| 4,800,883 | 1/1989 | Winstrom . |
| 4,880,005 | 11/1989 | Pless et al. . |
| 4,949,719 | 8/1990 | Pless et al. . |
| 4,953,551 | 9/1990 | Mehra et al. . |
| 5,088,488 | 2/1992 | Markowitz et al. . |
| 5,117,824 | 6/1992 | Keimel et al. . |
| 5,144,949 | 9/1992 | Olson . |
| 5,163,427 | 11/1992 | Keimel . |
| 5,188,105 | 2/1993 | Keimel . |
| 5,383,909 | 1/1995 | Keimel . |
| 5,545,186 | 8/1996 | Olson et al. . |
| 5,669,391 | 9/1997 | Williams ................................... 607/27 |
| 5,722,999 | 3/1998 | Ingu ......................................... 607/27 |

FOREIGN PATENT DOCUMENTS 9218198  10/1992  WIPO .

*Primary Examiner*—William E. Kamm
*Attorney, Agent, or Firm*—Reed A. Duthler; Harold R. Patton

[57] ABSTRACT

An implantable device which stores information indicative of events occurring within a patient's body and related to operation of the device for transmission to an external device in response to a request from the external device. The implanted device is provided with a mechanism for retaining information as to the state of the information stored in the device at the time of a preceding request or interrogation from the external device and for storing cumulative information indicative of the operation of the device or events occurring within the patient's body over a time frame spanning multiple interrogations or requests from the external device. The two types of stored information together may be employed by the implanted device or the external device to derive information indicative only of events occurring since a preceding interrogation of the implanted device by the external device.

8 Claims, 5 Drawing Sheets

IMPLANTABLE MEDICAL DEVICE WITH AUTOMATED LAST SESSION IDENTIFICATION

BACKGROUND OF THE INVENTION

This invention relates to implantable devices which detect and/or treat tachyarrhythmias (rapid heart rhythms), and more specifically, to mechanisms for monitoring the rhythm of the patient's heart and for monitoring the operation of the device.

In conjunction with monitoring the operation of an implantable device and the condition of the patient in whom the device is implanted, it has become common for the implanted device to keep records of and counts of events occurring during operation of the device. For example, as disclosed in U.S. Pat. No. 4,557,266 issued to Schober et al, the events counted may be as simple as delivered atrial and ventricular pacing pulses, sensed atrial and ventricular depolarizations, detected premature atrial and ventricular depolarizations and runs of premature depolarizations. In the context of implantable antitachyarrhythmia devices, it is common to maintain counts of the occurrences of the various arrhythmias detected by the device and counts of the various types of therapies employed by the device. It has also become common to retain measured parameters associated with operation of the devices, such as R-wave and P-wave amplitudes, battery voltage, lead impedance and the like, and in some cases to store information with regard to such parameters in the form of trend lines illustrating the values of the parameters over time, as disclosed in U.S. Pat. No. 5,088,488, issued to Markowitz et al.

These stored counts and/or measured parameters are typically provided to the physician during interrogation of the implanted device using an external programmer. In such cases, the implanted device uplinks the various stored counts and measured parameters since the last time the device memory was cleared. In some such devices, the various counts and/or stored parameters may be cleared by the physician in conjunction with interrogation of the device, so that upon subsequent interrogation, only the events occurring and values measured since the previous interrogation will be reflected in the stored information. This approach, however, results in the loss of the ability of the device to retain counts or values taken over an extended period of time, spanning multiple interrogation sessions. An additional alternative has been to employ time stamps in conjunction with the recording of the events occurring and parameters measured by the implantable device, so that the physician can determine, by comparing the time stamps to the time of the previous interrogation, which events occurred subsequent to the previous interrogation session.

SUMMARY OF THE INVENTION

The present invention is directed toward providing a simple and easy to use mechanism for providing values indicative of events occurring and parameters measured since the previous interrogation session, and to do so without losing information stored related to events occurring and parameters measured prior to the previous interrogation session. A device according to the present invention stores in memory the current values of information such as counts of events or measurements of parameters, which values are updated over a relatively long time frame spanning multiple interrogation sessions. At the end of each interrogation session, the device temporarily stores a duplicate copy of the then present values of the information separately, allowing the current values of the information to continue to be updated thereafter. After expiration of a predefined time period, for example 8 hours, the duplicate copy is permanently stored within the device as indicative of the values of the information at the end of the last interrogation session. On the next subsequent interrogation session, the device may telemeter the current values of the stored information related to events occurring or parameters measured prior to and after the previous interrogation session and/or, in response to a request, may also provide the values of information stored in conjunction with the end of the last interrogation session. This information may be employed by the external programmer to derive values corresponding only to events occurring since the last interrogation session. In an alternative embodiment, the implanted device may use the stored information to derive values associated only with events occurring or parameters measured since the last interrogation session and provide the derived values to the external programmer for display. The programmer or implanted device derives the values corresponding to events occurring since the last interrogation session by comparing the values stored in conjunction with the last interrogation session with the current values, to derive values indicative of the events occurring since the last interrogation session.

For example, the device may store a cumulative count of detected ventricular tachycardia episodes extending back to the initial implant of the device. The implanted device or external programmer may then compare this number to the cumulative count of ventricular tachyarrhythmia episodes stored in conjunction with the preceding interrogation, and from these two values derive a count of ventricular tachyarrhythmia episodes occurring since the last interrogation. Thus, the physician retains the ability to determine the occurrences of the various sorts of events tracked by the implantable device over a series of interrogation sessions, while being able to quickly and conveniently determine the more recent history of the device of the patient, since the last interrogation session. This feature allows the physician to more conveniently determine the effect of parameter changes which were made during the previous interrogation session. In addition, as the physician can conveniently review only the most recent performance of the device, the time required for follow-up and evaluation can be reduced.

DETAILED DESCRIPTION OF THE PREFERRED EMBODIMENTS

Figure 1:
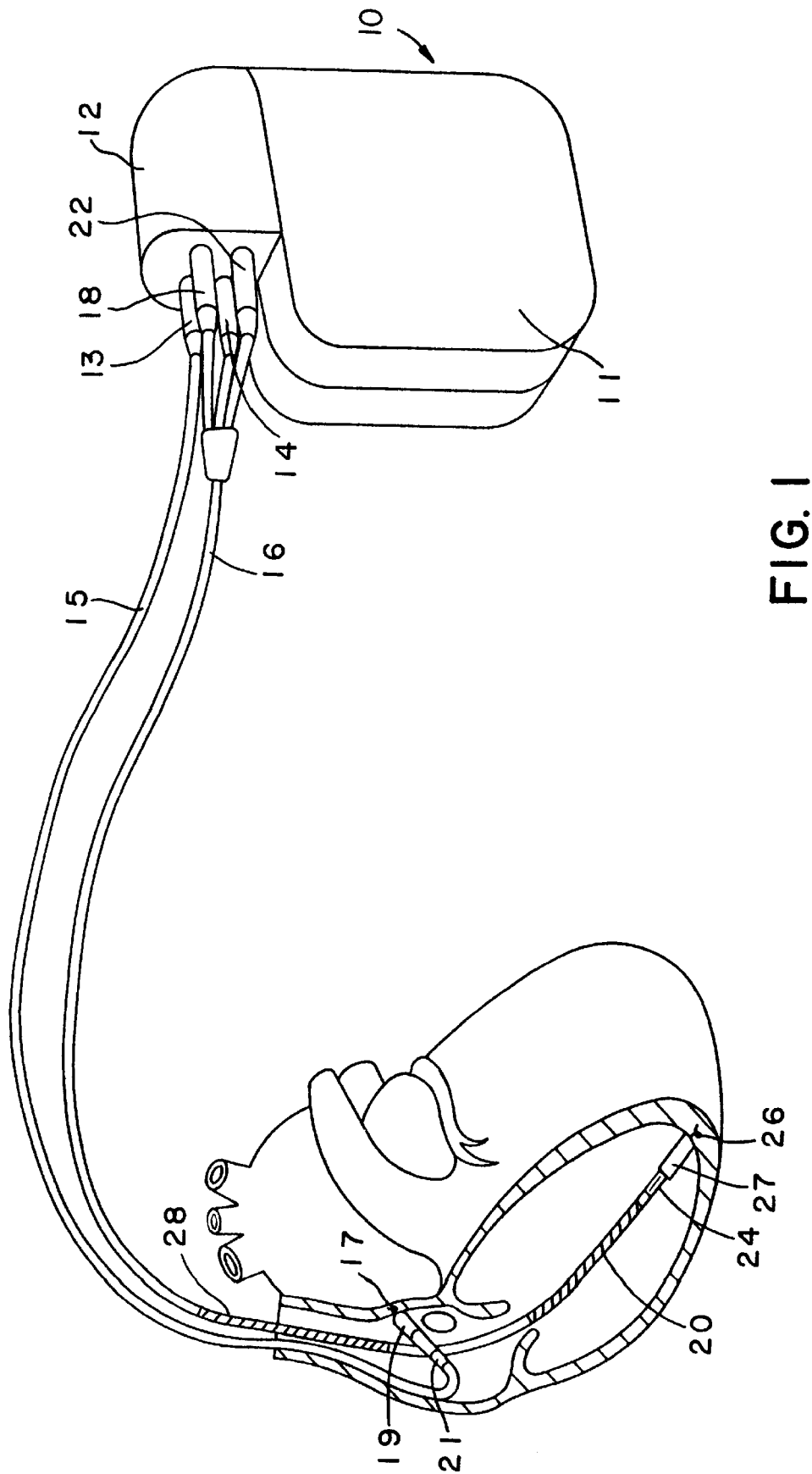
FIG. 1 illustrates an implantable pacemaker/cardioverter/defibrillator of a type appropriate for use in practicing the present invention, in conjunction with a human heart.

FIG. 1 illustrates a pacemaker/cardioverter/defibrillator 10 and lead set according to the present invention. The ventricular lead includes an elongated insulative lead body 16, carrying four mutually insulated conductors. Located on the lead body are a ring- electrode 24, an extendable helix electrode 26, mounted retractably within an insulative electrode head 27, and elongated coil electrodes 20 and 28. Each of the electrodes is coupled to one of the coiled conductors within the lead body 16. Electrodes 24 and 26 are employed for cardiac pacing and for sensing ventricular depolarizations. Electrodes 20 and 28 are employed in conjunction with the conductive housing 11 of the pacemaker/cardioverter/defibrillator 10 for delivery of ventricular cardioversion and defibrillation pulses. At the proximal end of the lead body 16 are two unipolar connectors 18 and 22 which each carry a connector pin coupled to one of the coiled electrodes 20 and 28. Electrical connector 14 is an in-line bipolar connector carrying a connector ring and a connector pin, coupled to electrodes 24 and 26, respectively.

The atrial lead as illustrated is a conventional bipolar atrial pacing lead. The atrial lead includes an elongated insulative lead body 15, carrying two concentric coiled conductors, separated from one another by tubular insulative sheaths. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atria] depolarizations. At the proximal end of the lead is an in-line connector 13 which carries a connector ring, and a connector pin, coupled to electrodes 21 and 17, respectively. In alternative lead systems, a defibrillation electrode, for example corresponding to electrode 28, might instead be mounted to the atrial lead, or might be mounted to a coronary sinus lead, for location in the coronary sinus and great cardiac vein.

An implantable pacemaker/cardioverter/defibrillator 10 is shown in combination with the leads, with the lead connectors 13, 14, 18 and 22 inserted into the connector block 12, which contains corresponding electrical connectors for coupling to the various connector rings and pins. Optionally, insulation of the outward facing portion of the housing 11 of the pacemaker/cardioverter/defibrillator 10 may be provided in the form of a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 serves as a subcutaneous defibrillation electrode, used in conjunction with one or both of electrodes 20 and 28.

Figure 2:
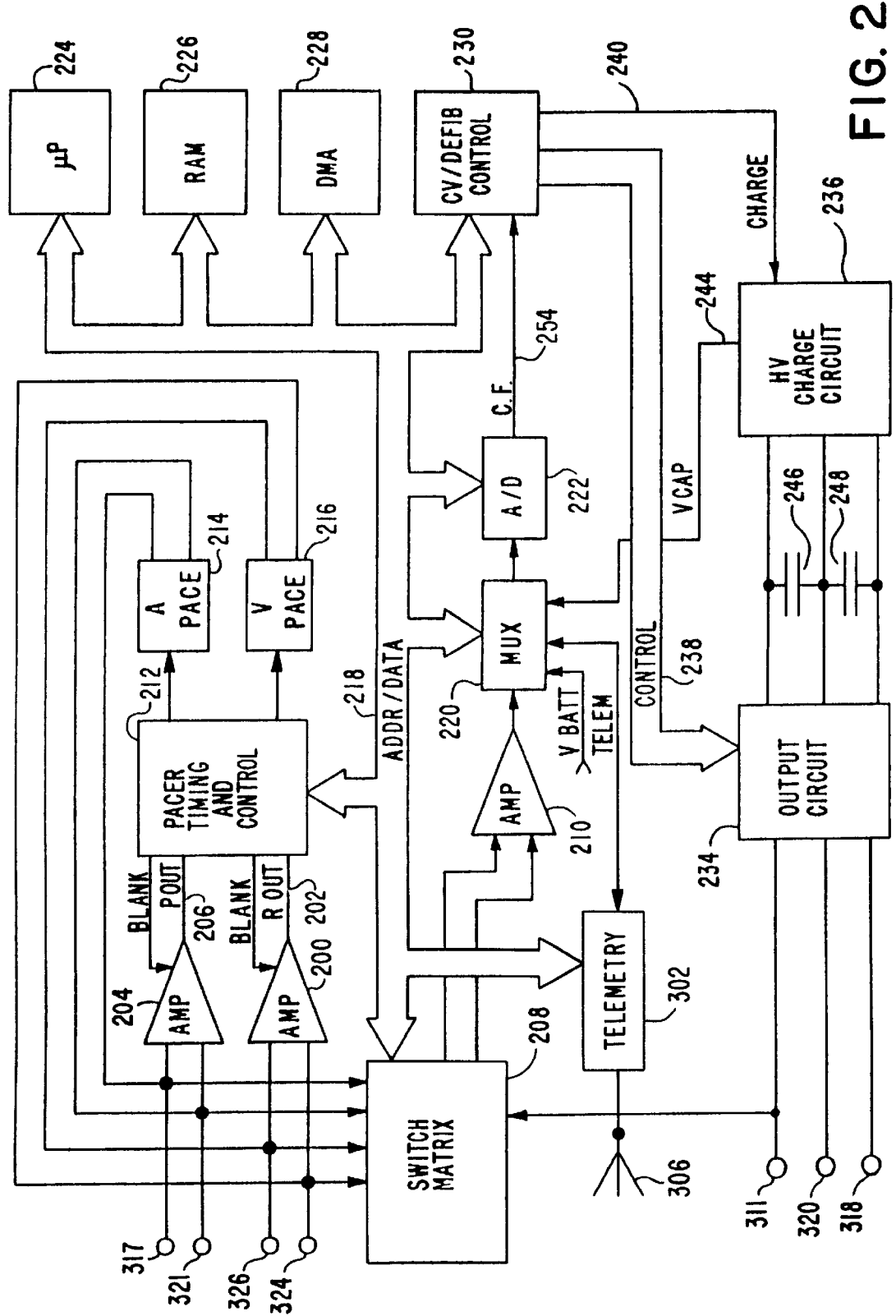
FIG. 2 illustrates a functional schematic diagram of an implantable pacemaker/cardioverter/defibrillator in which the invention may be practiced.

While the device disclosed herein includes both anti-tachycardia and anti-bradycardia therapies, the invention of course may be usefully practiced in devices including only anti-bradycardia therapies or only anti-tachycardia therapies. Similarly, while the device disclosed herein delivers electrical therapies to the heart, the invention FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide antitachycardia pacing therapies and antitachycardia pacers which do not provide cardioversion or defibrillation. The invention may also usefully be employed in devices which deliver other forms of therapies, such as implantable drug delivery devices, implantable nerve stimulators and implantable muscle stimulators, which also may benefit from the ability to store and retrieve information related to the patient's condition and/or the operation of the device.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter/defibrillator. Electrode 320 corresponds to electrode 20 and is a defibrillation electrode located in the right ventricle. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the 10 atrium.

Electrodes 311, 318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are located on or in the atrium and are coupled to the P-wave amplifier 204. which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and used to diagnose the occurrence of a variety of tachyarrhythmias.

Microprocessor 224 operates as an interrupt driven device operating under control of stored programming in a read only memory included therein. Microprocessor 224 is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be per-formed by microprocessor 224 and any updating of the values or intervals controlled by pacer timing/control circuitry 212 take place following such interrupts. A portion of the memory 226 (FIG. 4) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method employed in implantable anti-arrhythmia devices according to the present invention may be any of the tachyarrhythmia detection algorithms known to the art. In the particular embodiment discussed herein, the detection methodology disclosed in U.S. Pat. No. 5,545,186, issued to Olson et al. is employed to enable the device to detect and classify ventricular and supraventricular arrhythmias. In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 4,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Patent Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed, In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modem implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at antitachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, the typical therapy will be delivery of a high amplitude defibrillation pulse, typically in excess of 5 joules. Lower energy levels may be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

The device of FIG. 2 is provided with a telemetry circuit 302 which operates under control of microprocessor 224 via data/address bus 218 to receive commands and requests from an external programmer and to transmit data to an external programmer. Commands and requests from the external programmer are received via antenna 306, demodulated by telemetry circuit 302 and provided to microprocessor 224. Operational parameters controlling the operation of the device received from an external programmer are stored in designated locations in random access memory 226. In conjunction with the present application, the telemetry transmissions of interest include requests for uplink of stored values as described above, and the corresponding telemetry of the stored values to the external programmer.

The particular telemetry system employed to implement the invention is not critical to the success of the invention, and it is believed that the present invention may be practiced using any of the numerous known forms of bi-directional telemetry employed in the context of implantable pacemakers, defibrillators and other implantable electronic devices. For example, a telemetry systems as disclosed in U.S. Pat. No. 5,383,909 issued to Keimel may be employed.

Figure 3A:
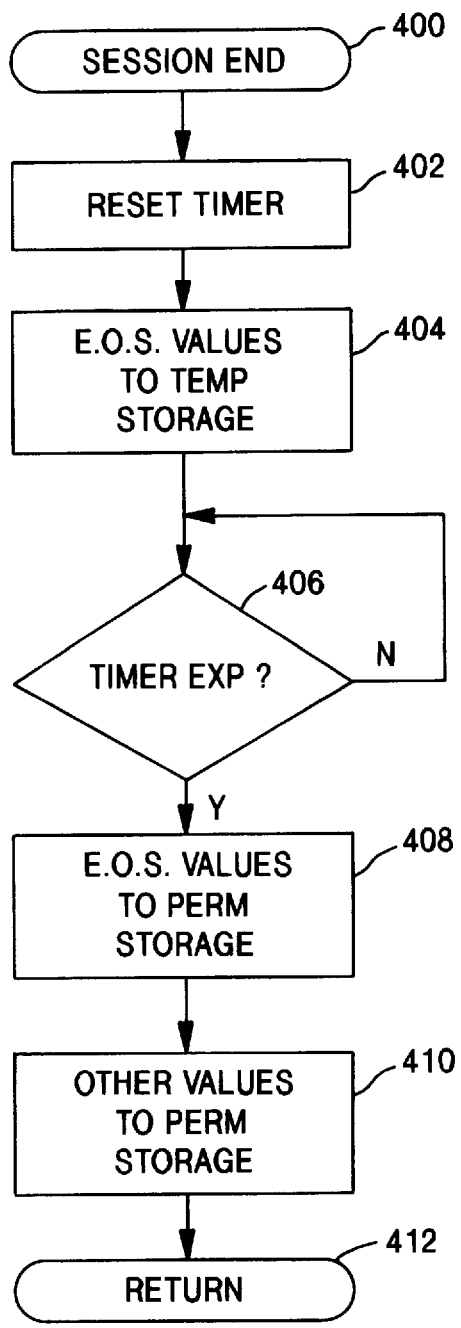
FIGS. 3A, 3B and 3C are functional flow charts illustrating the operation of the device in conjunction with the present invention.

FIG. 3A is a functional flow chart illustrating the overall operation of a device according to the present invention in response to the end of a programming/interrogation session conducted of the implantable device, by means of an external programmer. On end of the programming/interrogation session at 400, the microprocessor 224 resets an internal timer defined therein which may define a time interval which extends for a period of hours, for example, 8 hours, following the end of a session. The current value of the various stored counts and other values at the end of the session (EOS values) are stored at 404 in a set of memory locations in random access memory 226 reserved for their temporary storage. When the timer expires at 406, the values stored at the end of the session are transferred to a second set of memory locations in random access memory 226, for subsequent use in response to a request for values corresponding to events occurring since the last programming session. At 410, the device may optionally store the current values of other operational parameters or the values of other counts not stored at the end of the session at 404. The device then returns to normal operation at 412 until a subsequent interrogation/programming session.

In conjunction with the present invention, examples of the types of counts and values stored by the device for use in conjunction with the present invention may include cumulative counts of atrial sense ventricular sense sequences (AS-VS counter), a cumulative count of atrial sense ventricular pace event sequences (AS-VP counter), a cumulative count of atrial pace-ventricular sense event sequences (AP-VS counter), a cumulative count of atrial pace-ventricular pace event sequences (AP-VP counter), a cumulative count of premature atrial and/or ventricular beats defmed as a function of timing, a cumulative count of atrial and/or ventricular premature beat runs defined as a function of detected event timing, a cumulative count of hardware defined PVC's (ventricular sensed events not separated from a preceding ventricular event by an atrial event), and cumulative counts of each of the various types of tachyarrhythmias which the device is capable of identifying. For example, in the context of the device as described in the above cited Olson et al patent incorporated by reference, the device is capable of identifying episodes of ventricular tachycardia, fast ventricular tachycardia, ventricular fibrillation, supra-ventricular tachycardia, atrial fibrillation/flutter, sinus tachycardia and the like. Separate cumulative counts may be maintained for each such identified arrhythmia type.

If the device provides for measurement of battery voltage, lead impedance, R-wave and/or P-wave amplitudes and charge time data, the current values of these values and/or the current position of trend line type records of these values may also be saved at this time. If the device is provided with a mechanism for recording stored interval values and/or electrograms in conjunction with detection of arrhythmia episodes, the current status of such stored electrograms may also be included. For example, in the context of devices as manufactured by Medtronic, Inc., the device stores episode logs associated with detections of various types of tachycardias, and the current position of such episode logs may be stored in conjunction with the end of the interrogation/programming session. If the device is provided with the capability of performing mode switching, for example, as disclosed in U.S. Pat. No. 5,144,949 issued to Olson and incorporated by reference in its entirety, and stores a mode switch episode log in conjunction therewith, the current position of such episode log may also be stored. If the device is provided with a mechanism for retaining running storage of a preceding series of intervals between cardiac events, the current status of such a stored interval record may also be recorded, along with a time stamp indicating the time of occurrence of the end of the session. By this mechanism, the device can, if so requested, uplink only that portion of the episode log or stored series of intervals occurring since the last interrogation session, in conjunction with a request for information stored in conjunction with the end of the last session. Any other types of information stored by the device may also be stored in the defined memory locations in random access memory 226, at this time.

At 410, in addition to storing the above described values and information associated with the end of the interrogation session, the device may also store additional information indicative of the current state of cumulative counters at the end of the defined time period. For example, if not stored as part of the information indicative of the current values of the cumulative counters at the end of the session, the device might store, for example, cumulative counts of short atrial and ventricular intervals, for later use in diagnosing the operation of the device in the eight hour period immediately following the interrogation/programming session. This information may also be uplinked in response to a request by the external programmer for information associated with events occurring since the last interrogation/programming session. It is also contemplated that the physician may be able to determine, by means of an external programmer, which particular types of data are to have their values at the end of the interrogation session stored temporarily, and later moved to permanent storage and which types of values may be stored at the expiration of the defined time interval.

Figure 3B:
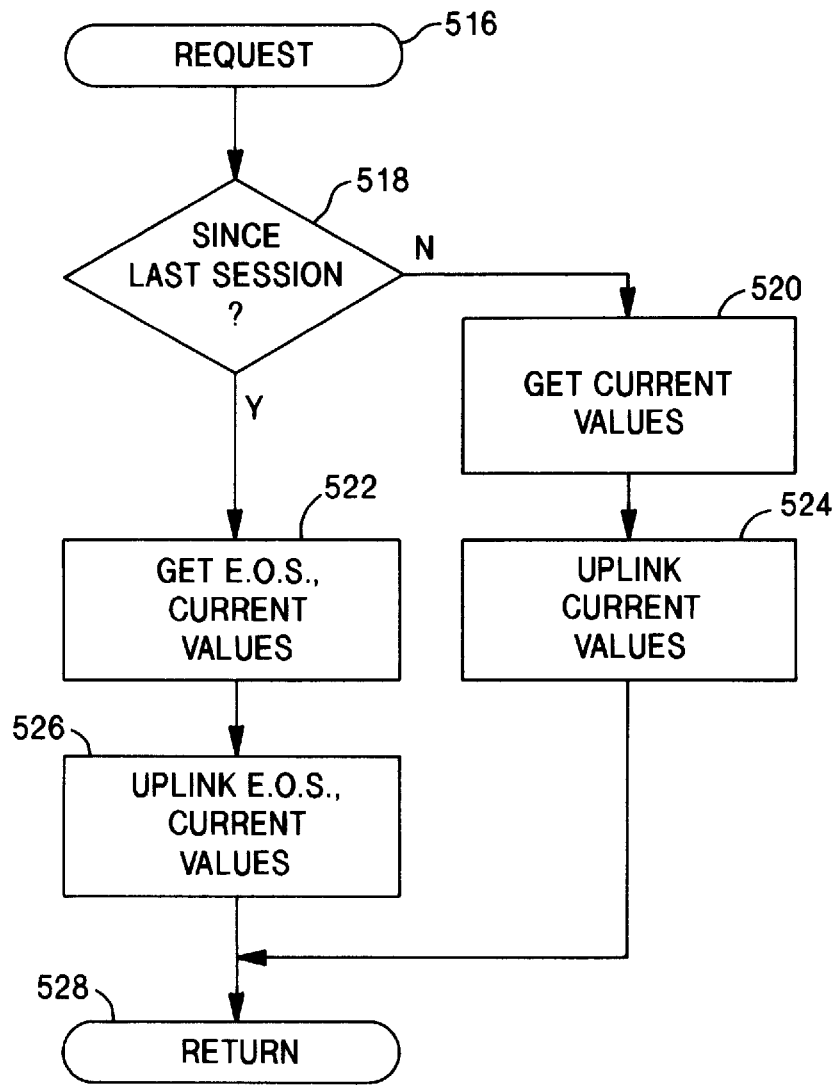

FIG. 3B illustrates the overall functional operation of the device according to a first embodiment of the invention in response to a request at 516 for uplink of information regarding the various stored values and counts. At 518, the microprocessor 224 determines whether the request is for values corresponding to events occurring since the last programming/interrogation session. If not, the device gets at 520 and uplinks at 524 the current, cumulative values, which may represent counts of events as described above which extend in time to a point previous to the last interrogation session, and may also include an uplink of the entire episode logs as described above, extending prior to the last interrogation session. For example, after implant, the counts of sequential atrial and ventricular events, referred to above may be initialized, which counts continue to run cumulatively until reset by means of an external programmer command. In response to the request for the cumulative value of such counts, the device at 524 would uplink the current values of the various counts, reflecting the numbers of such events occurring since the implant or reinitialization of the counts.

If, however, the request is for values corresponding to events occurring since the last programming/interrogation session, the microprocessor 224 retrieves the current values of the counts and values at 522, as well as the corresponding counts and values associated with the end of the last interrogation programming session. In addition, the device may employ the stored information as to the state of the episode logs to allow it to uplink only that portion of the episode logs or stored interval series occurring since the last interrogation session, which in turn shortens the transmission time required. These values are uplinked at 526 and the device returns to its normal operation awaiting the end of the programming/interrogation session then underway. It should also be understood that the stored values of and counts associated with the end of the last programming session, may themselves be directly uplinked if the physician so desires, as well as the values of information stored at the expiration of the defined time interval as discussed above.

Figure 3C:
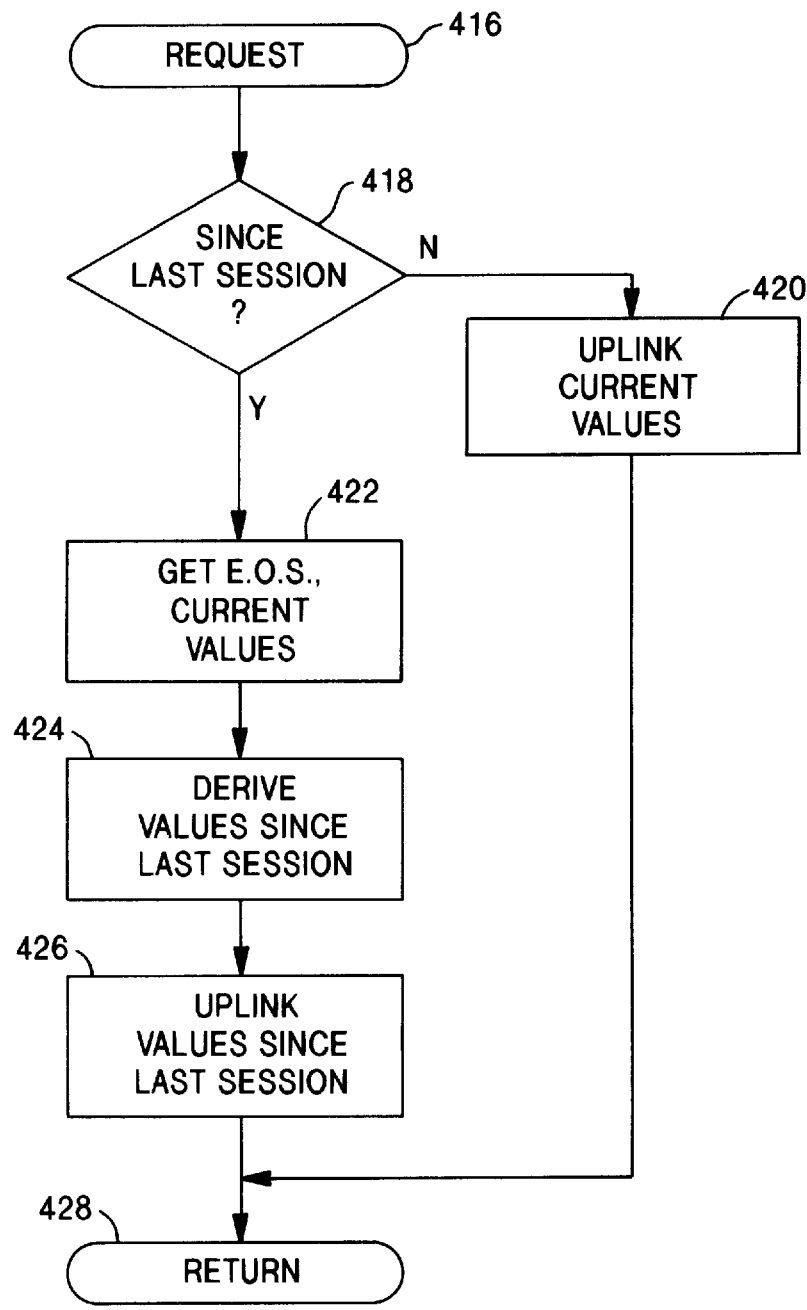

FIG. 3C illustrates the overall functional operation of the device according to a second embodiment of the invention in response to a request at 416 for uplink of information regarding the various stored values and counts. At 418, the microprocessor 224 determines whether the request is for values corresponding to events occurring since the last programming/interrogation session. If not, the device uplinks the current, cumulative values, which may represent counts of events as described above which extend in time to a point previous to the last interrogation session. For example, after implant, the counts of sequential atrial and ventricular events, referred to above may be initialized, which counts continue to run cumulatively until reset by means of an external programmer command. In response to the request for the cumulative value of such counts, the device at 420 would uplink the current values of the various counts, reflecting the numbers of such events occurring in an implant or reinitialization of the counts.

If, however, the request is for values corresponding to events occurring since the last programming/interrogation session, the microprocessor 224 retrieves the current values of the counts and values at 422, as well as the corresponding counts and values associated with the end of the last interrogation programming session. The microprocessor 224 processes these values at 424 to determine values/counts corresponding to events since the last programming/interrogation session. This processing may be, for example, simply subtracting the values of the counts described above stored at the end of the last interrogation/programming session with the current values of such counts, to derive counts of the corresponding events which occurred since the most recent programming/interrogation session. These new derived values are uplinked at 424 and the device returns to its normal operation awaiting the end of the programming/interrogation session then underway. In addition, the device may employ the stored information as to the state of the episode logs to allow it to uplink only that portion of the episode logs or stored series of intervals occurring since the last interrogation session, which in turn shortens the transmission time required. It should also be understood that the stored values of and counts associated with the end of the last programming session, may themselves be directly uplinked if the physician so desires, as well as the values of information stored at the expiration of the defined time interval as discussed above.

While the present invention is described in conjunction with an overall device configuration corresponding generally to that employed in implantable Medtronic pacemaker/cardioverter/defibrillators, it should be understood that the present invention may also be employed in conjunction with pacemakers, implantable defibrillators, and other implanted devices having substantially different configurations, so long as the device has the ability to store information with regard to events occurring cumulatively over a period of time and to telemeter information corresponding to this information in response to a request by an external programmer. The present invention is believed workable and valuable in any such device. Similarly, while the above disclosure lists a variety of stored information related to cumulative occurrences of events over time, with which the present invention may be practiced, it should be understood that the present invention can also be usefully practiced in conjunction with other types of stored information.

The present invention is believed particularly desirable for use in conjunction with a device which provides a therapy of some sort to the patient, such as delivery of an electrical therapy or a drug therapy, which therapy may also be modified by means of commands from an external programmer. In these devices, the capability of reviewing both the operation of the device and/or occurrences of the patient-related events over a relatively long time frame and to evaluate the operation of the device and the occurrence of such patient-related events since the alteration of operative parameters associated with the device is particularly valuable in assisting the physician in determining the appropriateness of changes to the device's operational settings occurring at a previous interrogation/programming session.

As such, the above disclosure should be considered exemplary, rather than limiting, with regard to the claims that follow.

In conjunction with the above disclosure

We claim:

1. A device for implantation within a patient's body, comprising:

means for detecting occurrences of events within said patient's body;

telemetry means for transmitting stored information from said device to an external device in response to requests from said external device;

first memory means for storing information with regard to occurrences of said events over a time period encompassing multiple requests from said external device for stored information;

second memory means for storing present values of said information stored in said first memory means at times of requests from said external device; and means responsive to a request from said external device for employing information stored in said first and second memory means to uplink information stored in said first and second memory means to said external device, whereby values with regard only to events occurring since a preceding request from said external device may be derived.

2. A device according to claim 1 further comprising:

temporary memory means for temporary storage of said present values of said information stored in said first memory means at times of requests from said external device; and a timer, defining a time period initiated in response to requests from said external device; and wherein said second memory means comprises means for storing information stored in said temporary memory means in response to expiration of said time period.

3. A device according to claim 2, further comprising fourth memory means for storing present values of events other than those stored in said first memory means; and wherein said second memory means comprises means for storing said present values of events other than those stored in said first memory means in said second memory means on expiration of said time period.

4. A device according to claim 1 or claim 2 or claim 3 wherein said information comprises numbers of occurrences of said events.

5. A device according to claim 4 wherein said events comprise multiple types of events and wherein said information comprises numbers of occurrences of said multiple types of events.

6. A device according to claim 1 or claim 2 or claim 3 wherein said values with regard only to events occurring since a preceding request from said external information comprises numbers of occurrences of said events since said preceding request.

7. A device according to claim 1 or claim 2 or claim 3 wherein said information comprises stored series of occurrences of said events.

8. A device according to claim 7 wherein said values with regard only to events occurring since a preceding request from said external information comprises a series of occurrences of said events since said preceding request.

* * * * *